United States Patent [19]

Sager

[11] Patent Number: 5,314,552

[45] Date of Patent: May 24, 1994

[54] BREAKAWAY PLUG ULTRASONICALLY BORED FROM FIRST THERMOPLASTIC PART & ULTRASONICALLY BONDED TO SURFACE OF SECOND THERMOPLASTIC PART

[75] Inventor: Thomas B. Sager, Newtown, Conn.

[73] Assignee: Branson Ultrasonics Corporation, Danbury, Conn.

[21] Appl. No.: 992,065

[22] Filed: Dec. 17, 1992

[51] Int. Cl.$^5$ .............................................. B32B 31/00
[52] U.S. Cl. ................................... 156/73.3; 156/253; 156/261; 156/294; 264/23
[58] Field of Search .................. 156/73.1, 73.3, 73.5, 156/252, 253, 261, 513, 580.1, 580.2, 293, 294; 264/23; 425/174.2

[56] References Cited

U.S. PATENT DOCUMENTS 5,118,370  6/1992  Ozawa ................................. 156/261

FOREIGN PATENT DOCUMENTS 2711305  12/1977  Fed. Rep. of Germany ........ 264/23
0340094  11/1989  France ............................... 156/73.1

Primary Examiner—David A. Simmons
Assistant Examiner—Mark De Simone
Attorney, Agent, or Firm—Polster, Lieder, Woodruff & Lucchesi

[57]     ABSTRACT

A method of providing an assembly of thermoplastic parts, which are separable upon the application of a predetermined force, includes assembling at least two thermoplastic parts in an overlapping relation and using an ultrasonically resonant horn for cutting a plug from the wall thickness of the first part and welding the plug to the underlying second part, whereby the upper portion of the plug remains surrounded by the wall of the aperture produced responsive to the cutting of the plug. Responsive to the application of a predetermined breakaway force effective on the plug, the plug breaks away from its attachment to the second part, causing the parts to become separable. The cross-sectional area of the plug is selected to meet a predetermined breakaway force requirement.

3 Claims, 1 Drawing Sheet

U.S. Patent    May 24, 1994    5,314,552
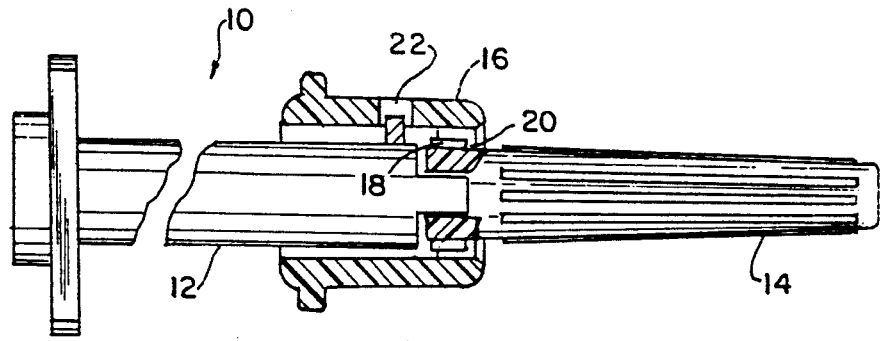
FIG.1.
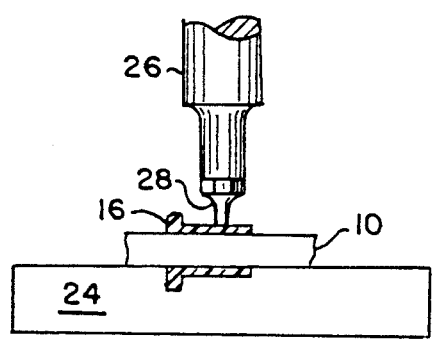
FIG.2.
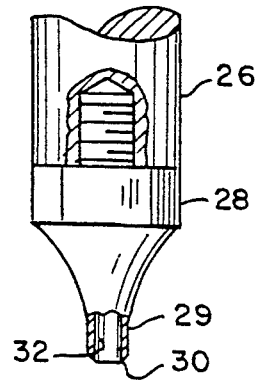
FIG.3.
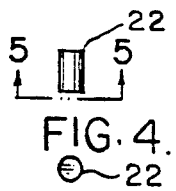
FIG.4.
FIG.5.
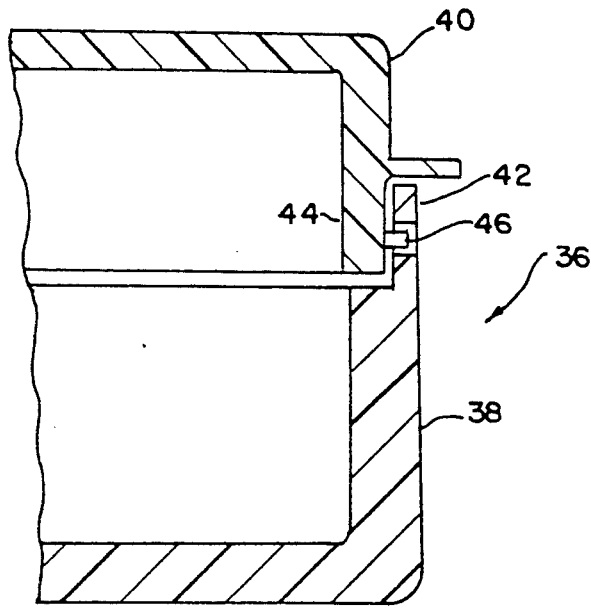
FIG.7.
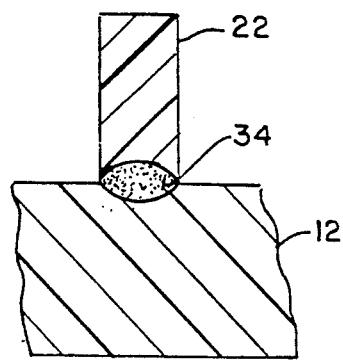
FIG.6.

BREAKAWAY PLUG ULTRASONICALLY BORED FROM FIRST THERMOPLASTIC PART & ULTRASONICALLY BONDED TO SURFACE OF SECOND THERMOPLASTIC PART

SUMMARY OF THE INVENTION

This invention concerns a method of providing an assembly of thermoplastic parts and, more specifically, refers to a method of providing an assembly of overlapping thermoplastic parts which are separable responsive to the application of a predetermined force. Quite specifically, this invention relates to a method of providing an assembly comprising at least two thermoplastic parts disposed in an overlapping relation and cutting a plug of predetermined cross-section from one of the parts and welding the plug with its surface confronting the other part to such other part, whereby a portion of the plug remains surrounded by a portion of the part from which the plug has been cut. Responsive to the application of a breakaway force effective upon the plug, the plug breaks away from such other part, thus causing the assembly to become separable.

In the preferred method, cutting the plug from the first par and welding it to an underlying second part is accomplished by high frequency vibrations in the ultrasonic frequency range provided by a horn rendered resonant and brought into forced contact with the first part for cutting the plug from such first part, and then causing the horn to remain in contact with the plug for welding the plug to the second part. When there exists a gap between the first part and the second part, the horn moves the plug across such gap prior to welding the plug to the underlying second part.

The breakaway force for breaking the plug away from its attachment to the second part for causing the assembly to become separable is predetermined since the force required is a function of the welded area between the plug and the second part, which, in turn, is a function of the cross-sectional area of the plug. Therefore, by cutting a plug of predetermined cross-section from the first part, the break-away force becomes predetermined.

An assembly of this type is eminently suited for assuring the integrity of a package and its contents. If the plug is in place, the assembly is locked, but if a force of predetermined size has been applied and the plug has broken away causing the assembly to become separable, the integrity of the package and its contents is in doubt.

One of the principal objects of this invention is a method for providing an assembly of thermoplastic parts separable responsive to the application of a predetermined force.

Another important object of this invention is a method for providing an assembly of thermoplastic parts separable responsive to the application of a predetermined force by cutting a plug of predetermined cross-section from a first part and welding it to an underlying second part, the plug remaining surrounded by a portion of the first part.

Another important object of this invention is a method for providing an assembly of thermoplastic parts in overlapping relation and separable responsive to the application of a predetermined force, wherein ultrasonic frequency vibrations are used to cut a plug from a first thermoplastic part and weld such plug to an underlying second thermoplastic part.

Still another object of this invention is a method of providing an assembly of thermoplastic parts separable responsive to the application of a predetermined force, wherein a horn rendered resonant at an ultrasonic frequency is used to cut a plug of predetermined size from a first thermoplastic part and weld the separated plug to an under-lying second thermoplastic part.

A further object of this invention is the provision of a package comprising an assembly of thermoplastic parts, the integrity of which is readily established.

Still further and other objects of this invention will become more clearly apparent by reference to the following description when taken in conjunction with the accompanying drawings.

BRIEF DESCRIPTION OF THE DRAWING

FIG. 1 is a side elevational view, partly in section, of a completed assembly of thermoplastic parts produced in accordance with the invention;

FIG. 2 is a schematic illustration showing the apparatus for producing the assembly shown in FIG. 1;

FIG. 3 is a view, partly in section, of a horn tip for cutting a plug from one thermoplastic part and welding the plug to the underlying other part;

FIG. 4 is an elevational view of a typical plug cut from one of the thermoplastic parts;

FIG. 5 is a view of the plug along lines 5—5 in FIG. 4;

FIG. 6 is an explanatory sketch for depicting the weld between the plug and the part to which the plug is welded, and FIG. 7 is an elevational view, partly in section, of another assembly of thermoplastic parts in accordance with the invention.

DETAILED DESCRIPTION OF THE INVENTION

Referring now to the figures and FIG. 1 in particular, there is shown for illustrative purposes a thermoplastic syringe assembly 10 comprising a cylindrical thermoplastic barrel 12 which is in telescopic engagement with a sheath 14, also made of thermoplastic material. A collar 16 of thermoplastic material is provided to slip over the sheath 14 and, when secured upon the barrel 12 in accordance with the present invention to establish the integrity of the assembly. Numerals 18 and 20 designate upstanding projections from the sheath 14 and collar respectively, thereby providing a small annular gap between the barrel and the collar. The projections 18 and 20 are so dimensioned that when the collar 16 is assembled in overlapping relationship with the barrel 12 and secured to the underlying barrel 12, the barrel 12 and the sheath 14 cannot be separated from one another without destroying the attachment between the collar 16 and the barrel 12. The projections, while interfitting, permit limited rotational movement between the sheath 14 and the barrel 12 absent the collar 16 being secured to the barrel 12.

In accordance with the invention, a cylindrical plug 22 has been cut from the collar 16, moved across the air gap between the collar 16 and barrel 12, and the lower end surface of the plug 22 confronting the barrel 12 has been welded to the barrel 12. The upper portion of the plug 22 remains surrounded by the collar 16, i.e. the wall of the aperture created by the cutting of the plug. In that state, the integrity of the assembly is clearly visible. For causing the barrel 12 to become separable from the sheath 14, a predetermined force is required to be applied to cause the plug 22 to break away from the barrel 12, thereby freeing the collar 16. Such breakaway force is readily applied by a rotational force between the barrel 12 and the sheath 14, causing the plug 22 to break away from its attachment to the barrel 12 as a result of the aperture wall of the collar 16 exerting a force against the upper portion of the plug 22. It will be apparent, referring to FIGS. 4 and 5, that the axial length of the plug 22 is equal to the wall thickness of the collar 16 and that the cross-sectional area of the plug 22, by virtue of the weld area, determines the breakaway force required to separate the plug from its attachment to the barrel 12. As the barrel 12 and sheath 14 are urged into rotation relative to one another, the projections between the collar 16 and the sheath 14 cause the collar to exert the breakaway force upon the plug 22.

FIGS. 2 and 3 show the apparatus for carrying out the method described above. Numeral 10 designates the assembly of thermoplastic parts substantially as described in connection with FIG. 1, and numeral 16 designates the collar. The assembly 10 is supported on a suitable anvil 24. A horn 26, rendered resonant as a half wavelength resonator along its longitudinal axis at a predetermined ultrasonic frequency, typically in the range between 16 and 60 kHz, is lowered upon the assembly for causing the front end of the horn 26 to cut a plug 22 from the wall thickness of the collar 16, retain the plug 22 while advancing toward the underlying barrel 12, FIG. 1, weld the lower end of the plug to the barrel, and remain in forced engagement with the plug and the barrel for a brief dwell period during which the vibrations have ceased to permit the softened and flowed thermoplastic material at the interface between the plug 22 and barrel 12 to rigidify for forming a weld. The horn 26 is then withdrawn, leaving the plug 22 free standing, but welded to the barrel 12. The horn 26 at its upper end is mechanically coupled to an electroacoustic transducer which, in turn, receives electrical energy at the predetermined high frequency from an electrical power supply, all as is well known in the art.

Cutting of the plug 22 is accomplished by a tip 28, forming a part of the horn 26, which is threadedly attached to the horn 26 and forms the front end of the horn. As seen, the tip 28 is provided with a thin wall cylindrical section 29 having a sharp cutting edge 30 and a bore 32 for receiving therein the material forming the plug. The axial depth of the bore is substantially equal to the thickness of the wall from which the plug is cut, but experiments have shown that the bore, suitably, can be about one millimeter longer than the wall thickness from which the plug is cut using, for example, bores of 1.37, 1.72 and 1.93 mm diameter. It will be apparent that plugs do not need to be of cylindrical shape, although round bores are produced more easily. As previously stated, the cross-section of the plug can be selected to require a predetermined breakaway force. As the plug is cut responsive to forced engagement between the horn 26 and the collar 16, the thermoplastic material forming the plug 22 enters the bore 32 of the tip 28 and is carried by the horn toward the underlying part to which the plug is to be welded. Welding occurs responsive to the dissipation of vibratory energy while there is forced contact between the plug 22 and the part to which the plug is to be welded. The gap between the parts, quite clearly, must be smaller than the length of the plug, which, in turn, is given by the thickness of the part providing the plug.

FIG. 6 illustrates the weld area 34 formed between the plug 22 and the barrel 12, Responsive to the application of the breakaway force, the plug most commonly breaks away in the region of the weld.

FIG. 7 illustrates another example of the invention. A box 36 comprises a bottom portion 38 and a lid 40, both made of compatible thermoplastic material. The lid is hinge mounted to the bottom portion 38 at the left end of FIG. 7, not shown. The bottom portion is provided with a flange 42 which overlaps the lower end of the lid 40. Using the apparatus shown heretofore a plug 46 has been cut from the flange 42, transported across the gap between the flange 42 and the lid 40 and welded to the lid. In order to gain access to the contents of the box 36, it is necessary to raise the lid 40. As the lid is raised, the upper portion of the plug 46 becomes engaged by the aperture wall produced in the flange responsive to cutting the plug 46 from the flange 42, thus causing a breakaway force to be applied to the plug 46 and, upon the force attaining a predetermined value, the plug will separate from its attachment to the lid 40. In this manner, the absence of the plug 46 is indicative of the fact that the box no longer is in an uncompromised state.

It will be apparent that the disclosed method is applicable to many similar assemblies of thermoplastic parts where the integrity of the assembly or contents is of importance.

While there have been described and illustrated typical embodiments of the present invention, it will be apparent to those skilled in the art that various further changes and modifications can be made without departing from the broad principle of this invention, which shall be limited only by the scope of the appended claims.

What is claimed is:

1. The method of providing an assembly of thermoplastic parts separable responsive to the application of a predetermined force upon a breakaway plug comprising:

assembling a first thermoplastic upper part in an overlapping relation upon a second thermoplastic lower part;

providing a horn rendered resonant as a half wavelength resonator at an ultrasonic frequency and having at its free frontal end a bore, the depth of which is substantially equal to the thickness of the material of said first part at the isolation where said horn is intended to engage said first part;

providing forced engagement between said horn and said first part at said location and causing said horn to penetrate into said first part, causing thermoplastic material to be cut from said first part and enter into said bore for forming a solid plug, whereby leaving a cavity in said first part;

continuing motion of said horn toward the underlying second part until the end surface of said plug confronting said second part is in contact with said second part for welding said plug to the surface of said second part;

maintaining for a brief time interval said horn at the position at which there is contact between said end surface of said plug and said second part; ceasing the horn to be resonant for causing softened and flowed thermoplastic material, produced at the interface between said plug and said second part responsive to the dissipation of vibratory energy, to rigidify;

withdrawing said horn from said second part and said first part whereby to leave said plug free-standing but welded to said second part with the wall of the aperture produced in said first part responsive to cutting said plug surrounding a portion of said plug, and whereby, responsive to a predetermined breakaway force applied between said wall of said aperture and said plug, said plug breaks away from its attachment to said second part, thereby rendering said first part and said second part separable.

2. The method of providing an assembly of thermoplastic parts as set forth in claim 1, said bore being cylindrical, causing said plug to have a cylindrical cross-section and said aperture to be cylindrical.

3. The method of providing an assembly of thermoplastic parts as set forth in claim 2, said first part and said second part being cylindrical parts assembled, at least in part, upon one another.

* * * * *

UNITED STATES PATENT AND TRADEMARK OFFICE
CERTIFICATE OF CORRECTION

PATENT NO. : 5,314,552
DATED : May 24, 1994
INVENTOR(S) : Thomas B. Sager

It is certified that error appears in the above-indentified patent and that said Letters Patent is hereby corrected as shown below:

Column 1, Line 26 delete "par" and insert -- part --
Column 4, Line 48 delete "isolation" and insert -- location --

Signed and Sealed this

Sixth Day of December, 1994

Attest:

BRUCE LEHMAN

*Attesting Officer*    *Commissioner of Patents and Trademarks*